United States Patent [19]

Brooker et al.

[11] Patent Number: 4,479,960

[45] Date of Patent: Oct. 30, 1984

[54] ANTHELMINTHIC POUR-ON VETERINARY COMPOSITION

[75] Inventors: Peter J. Brooker; John Goose, both of Saffron Walden, England

[73] Assignee: Bayer AG, Bayerwerk, Fed. Rep. of Germany

[21] Appl. No.: 522,730

[22] Filed: Aug. 12, 1983

Related U.S. Application Data

[60] Division of Ser. No. 327,742, Dec. 4, 1981, Pat. No. 4,414,222, which is a division of Ser. No. 832,916, Sep. 13, 1977, Pat. No. 4,336,262, which is a division of Ser. No. 773,111, Feb. 28, 1977, Pat. No. 4,070,467, which is a continuation of Ser. No. 443,552, Feb. 19, 1974, abandoned.

[30] Foreign Application Priority Data

Feb. 23, 1973 [GB] United Kingdom ............... 8972/73
Jan. 25, 1974 [GB] United Kingdom ............... 3521/74

[51] Int. Cl.$^3$ ............................................. A61K 31/425
[52] U.S. Cl. ................................... 424/270; 424/358
[58] Field of Search ........................................ 424/270

[56] References Cited

U.S. PATENT DOCUMENTS 3,980,791 9/1976 Schulz et al. ...................... 424/270

Primary Examiner—Sam Rosen
Attorney, Agent, or Firm—Wenderoth, Lind & Ponack

[57] ABSTRACT

A new technique for combating helminthic parasites in an animal, e.g. a sheep or cow, comprises applying to the skin of the animal an anthelmintic amount of an anthelmintic compound, e.g. 4,5,6-trichloro-7-(diethylsulphamoyl)-2-(trifluoromethyl) benzimidazole, whereby the compound is absorbed by the animal through its skin.

17 Claims, No Drawings

ANTHELMINTHIC POUR-ON VETERINARY COMPOSITION

This is a divisional application of Ser. No. 327,742, filed Dec. 4, 1981, now U.S. Pat. No. 4,414,222, which in turn is a divisional application of Ser. No. 832,916, filed Sept. 13, 1977, now U.S. Pat. No. 4,336,262, which is a divisional application of Ser. No. 773,111, filed Feb. 28, 1977, now U.S. Pat. No. 4,070,467, which is a continuation of Ser. No. 443,552, filed Feb. 19, 1974, now abandoned.

This invention relates to parasiticides.

It is well known to combat helmintic parasites in animals by administering chemicals to the animals. The chemicals are administered either orally or by injection. We have now discovered an entirely new and yet simple and advantageous way of treatment, by external application.

Accordingly, the invention provides a method of combating helminthic parasites in an animal, which method comprises applying to the skin of the animal an anthelmintic amount of an anthelmintic compound, whereby it is absorbed by the animal through its skin.

The invention provides also an anthelmintic composition for application to the skin of an animal, which composition comprises the compound in a carrier effective for passing the compound through the skin of the animal.

The present technique makes it easier to ensure an accurate dose than when an anthelmintic is added to the animal's food or water supply. It avoids the possibility of inhalation or subsequent expulsion when an anthelmintic is applied directly into the mouth of the animal. It is rapid and easy to use. It is not necessary to sterilize materials as is the case when an anthelmintic is applied by injection, and a wider range of cheaper carriers can be employed than in compositions for use by injection. It also avoids any local reaction which may be set up in some animals, e.g. some cattle, around the point of injection. In addition, it can provide sustained absorption of the anthelmintic, resulting in a more favourable therapeutic ratio.

Compounds which may be administered by the present technique include those commercially available anthelmintic compounds (i.e. compounds which kill helminthic parasites) heretofore administered by injection. Most of the compounds which have good activity when administered by injection also have good activity when administered by the present technique. Commercially available anthelmintic compounds heretofor administered orally may also be employed, though naturally not any chemicals administered orally which rely on being converted to the anthelmintic compound on passage through the animal's food pathways. Suitable anthelmintic compounds include Tetramisole (2,3,5,6-tetrahydro-6-phenylimidazo[2,1-b]thiazole especially the laevo isomer, or a salt thereof), Thiabendazole [2-(4-thiazolyl)benzimidazole or a salt thereof], carbon tetrachloride, Parbendazole (methyl 5-butyl-benzimidazole-2-carbamate or a salt thereof), Hexachlorophene [2,2'-methylenebis-(3,4,6-trichlorophenol) or a salt thereof], Methyridine [2-(2-methoxyethyl)pyridine or a salt thereof], Nitroxynil (4-hydroxy-3-iodo-5-nitrobenzonitrile or a salt thereof), Rafoxanide [3'-chloro-4'-(p-chlorophenoxy)-3,5-diiodosalicylanilide or a salt thereof], Oxyclozanide (3,3',5,5',6-pentachloro-2,2'-dihydroxy-benzanilide or a salt thereof), Benomyl (methyl 1-[butylcarbomoyl]benzimidazole-2-carbamate), Bavistin (methyl benzimidazole-2-carbamate or a salt thereof), Thiophanate (diethyl 4,4'-o-phenylenebis[3-thioallophanate]), Oxibendazole (methyl 5-propoxybenzimidazole-2-carbamate or a salt thereof), triphenylbismuth, triphenylbismuth dinitrate, triphenylbismuth dichloride, and triphenylbismuth difluoride, and especially the first mentioned.

Particularly in the present technique there may be used an anthelmintic compound which is a substituted benzimidazole of formula

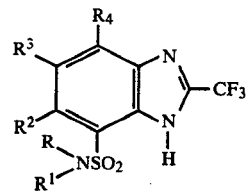

in which
R represents hydrogen or alkyl of 1 to 12 carbon atoms and $R^1$ represents alkyl of 1 to 12 carbon atoms, or R and $R^1$, together with the nitrogen atom to which they are attached, form a heterocyclic ring; and
$R^2$, $R^3$ and $R^4$, which are the same or different, each represent a halogen atom;
or a salt of this substituted benzimidazole.

Preferably $R^2$, $R^3$ and $R^4$, which are the same or different, each represent a chlorine or bromine atom.

When R or $R^1$ represents an alkyl group of 1–12 carbon atoms, it is preferably of 1–6 carbon atoms, e.g. methyl or ethyl, especially ethyl.

When R and $R^1$, together with the nitrogen atom to which they are attached, form a heterocyclic ring, it can be for example a 5 or 6 membered ring, usually containing one nitrogen or one nitrogen and one oxygen atom as the hetero atoms in the ring and generally saturated. For example, it may be piperidino or morpholino.

Thus, preferably R represents hydrogen or alkyl of up to 6 carbon atoms and $R^1$ represents alkyl of up to 6 carbon atoms, or R and $R^1$, together with the nitrogen atom to which they are attached, form a piperidino radical; and
$R^2$, $R^3$ and $R^4$, which are the same or different, each represent a chlorine or bromine atom.

An especially preferred group of these compounds are those where R and $R^1$ each represent an ethyl group and $R^2$, $R^3$ and $R^4$, which may be the same or different, each represent a chlorine or bromine atom.

Particularly preferred specific compounds are:
4,5,6-trichloro-7-(diethylsulphamoyl)-2-(trifluoromethyl)benzimidazole;
4-bromo-5,6-dichloro-7-(diethylsulphamoyl)-2-(trifluoromethyl) benzimidazole;
4,5,6-tribromo-7-(diethylsulphamoyl)-2-(trifluoromethyl)benzimidazole;
4,6-dibromo-5-chloro-7-(diethylsulphamoyl)-2-(trifluoromethyl) benzimidazole;
4,5,6-trichloro-7-(ethylsulphamoyl)-2-(trifluoromethyl)benzimidazole;
4,5,6-trichloro-7-(methylsulphamoyl)-2-(trifluoromethyl)benzimidazole;
4,5,6-trichloro-7-(n-propylsulphamoyl)-2-(trifluoromethyl)benzimidazole;
and especially the first mentioned; and their salts.

It will be appreciated that the present substituted benzimidazole may be in the form of a salt. The salt should clearly not be any such as would harm the particular animal being treated. Salts which may be formed by reason of the imidazole part of the molecule include ammonium salts, metal salts such as for example sodium, potassium, calcium, zinc, copper and magnesium salts, and amine salts such as for example methylamine, ethylamine, dimethylamine, triethylamine, ethanolamine, triethanolamine and benzylamine salts. According to a preferred embodiment any salts are alkali metal salts or N-methyl-glucamine salts.

The salts may be prepared by reacting the substituted benzimidazole in aqueous or aqueous-organic solvent solution or suspension with an alkaline compound of the metal, such as the hydroxide, or with the amine or ammonia, as appropriate. The metal salts may also be prepared by metathesis for example between the alkali metal salt of the benzimidazole and a salt of the metal. Some of the benzimidazoles are also basic by reason of the $SO_2NRR^1$ part of the molecule and can form salts with strong acids such as hydrochloric acid.

The present method is preferably applied to mammals especially those which are domestic or farm animals, such as sheep, pigs, domestic bovine animals (i.e. cattle), horses, goats, dogs and cats. It may also be applied to human beings. It may be applied also to animals used in laboratories, such as rats, mice and guinea pigs. The compound may be used to inhibit infection or to treat an infection already present.

Those anthelmintics which can exist in the form of salts, (for example 2,3,5,6-tetrahydro-6-phenylimidazo(2,1-b)thiazole) have generally been found to be much more effective in the process and composition of the present invention when used in non-salt form. In a preferred embodiment, the non-salt form of such anthelmintics is employed.

The anthelmintic activity of 2,3,5,6-tetrahydro-6-phenylimidazo (2,1-b)thiazole and its salts is believed to lie almost entirely in the laevo isomer. Thus, in a preferred embodiment, the laevo isomer is employed. However a mixture of the optical isomers (e.g. the racemate) may be used where convenient.

In the present technique, the animal absorbs the compound through its skin. The compound is usually applied in a composition containing a carrier. A wide range of appropriate carriers may be employed. The composition may be a cream. A liquid composition, however, is particularly convenient to use, e.g. facilitating measuring out doses, and facilitates absorbance through the skin. Thus, a solution or suspension of the compound in a liquid carrier is preferred. Solutions are especially good for transmitting the compound through the skin and are therefore most preferred. The liquid carrier preferably comprises one or more liquids selected from hydrocarbons (e.g. aromatic hydrocarbons such as an aromatic hydrocarbon fraction of boiling point 130°–250° C. e.g. 180°–220° C., xylene, benzene or toluene, or paraffins such as those of 6–20 carbon atoms), halogenated aliphatic hydrocarbons (e.g. carbon tetrachloride), ketones (e.g. cyclohexanone or 2-butanone), esters (e.g. ethyl acetate, ethyl benzoate or triacetin), ethers (e.g. diisopropyl ether or tetrahydrofuran), alcohols (e.g. alkanols of 2–8 carbon atoms such as butyl alcohol, amyl alcohol or isopropyl alcohol, or glycols such as monopropylene glycol), amides (e.g. dimethylformamide), sulphones (e.g. dimethyl sulphone or sulpholane) and sulphoxides (e.g. dimethyl sulphoxide). In many cases a mixture of liquids is desirable. Results vary depending on the particular carrier employed and an excellent carrier for one compound may not be for another. Any envisaged carrier can of course readily be tested by routine experiment, usually initially on laboratory animals such as mice or rats, and generally a good degree of correlation had been found between results on such laboratory animals and results on farm animals such as sheep and cattle. Results on one species may not however be duplicated on another. Preferably the liquid carrier comprises one or more liquids selected from hydrocarbons (e.g. aromatic hydrocarbons), alcohols (e.g. isopropyl alcohol or amyl alcohol) and sulphoxides (e.g. dimethyl sulphoxide). The invention provides particularly a liquid anthelmintic composition for use by external application to the animal, which composition comprises a solution or suspension of the compound in a carrier comprising at least one of dimethyl sulphoxide and amyl alcohol, preferably both. A mixture of dimethyl sulphoxide and amyl alcohol is especially valuable as carrier. Thus a specific composition comprises a solution of 4,5,6-trichloro-7-(diethylsulphamoyl)-2-(trifluoromethyl)benzimidazole in a carrier comprising a mixture of dimethyl sulphoxide and amyl alcohol.

Besides the compound and the carrier which is effective for passing the compound through the skin of the animal, the composition may contain additives e.g. to facilitate use on the animal. For example, the composition may contain additives to facilitate contact with the skin of the animal, to protect the skin from any undesirable action e.g. irritation otherwise caused by the carrier, or to improve retention of the composition on the animal.

The viscosity of liquid compositions may be increased over what it would otherwise be, by including thickeners, which increase the viscosity. This may be desirable in order to retard or prevent the composition from running off the animal.

The additives may include for example a surface active agent, an animal fat or wax, e.g. lanolin, a mineral oil, e.g. liquid paraffin, a vegetable oil, e.g. peanut oil, olive oil, corn oil or castor oil, or a polymer, e.g. a hydrocarbon polymer such as polyisobutene.

The surface active agents may comprise anionic compounds for example soaps, fatty sulphate esters such as dodecyl sodium sulphate, fatty aromatic sulphonates such as alkyl-benzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise non-ionic surface active agents such as for example condensation products of fatty acids, fatty alcohols or fatty substituted phenols with ethylene oxide or fatty esters and ethers of sugars or polyhydric alcohols, or the products obtained from the latter by condensation with ethylene oxide, or the products known as block copolymers of ethylene oxide and propylene oxide. The surface active agents may also comprise cationic agents such as for example cetyl trimethylammonium bromide.

The term "surface active agent" is used in the broad sense to cover materials variously called wetting agents, emulsifying agents and dispersing agents.

The composition may contain substances whose taste deters other animals from licking the composition off the animal treated. An example of such a substance is bitter aloes.

Generally additives facilitating the use in pour-on formulations of other materials, e.g. systemic insecticides, active on animal physiology may be of use also in the present composition.

The composition may contain other materials which stimulate the health of the animal, e.g. systemic materials which can themselves be employed as pour-on formulations. Thus, materials which combat ectoparasites, e.g. lice, ticks or warble fly, such as Famphur (0-[p-(dimethylsulphamoyl)phenyl]0,0-dimethyl phosphorothioate), may be present.

A single material may function in more than one respect e.g. it may protect the skin and enhance retention.

A preferred composition is a solution comprising 2,3,5,6-tetrahydro-6-phenylimidazo(2,1-b)thiazole, cyclohexanone, aromatic hydrocarbon (e.g. aromasol) and vegetable oil (e.g. corn oil). Another preferred composition is a solution comprising 2,3,5,6-tetrahydro-6-phenylimidazo(2,1-b)thiazole, dimethyl sulphoxide, amyl alcohol and optionally vegetable oil.

The particular additives and their amounts which are employed depend on the particular compound and treatment. Generally, however, the composition may consist by weight of ½-95% of the compound, 5-99½% of the carrier and 0-60% of additive, usually 1-15%, e.g. 1-10% of the compound, 45-99% of the carrier and 0-60%, e.g. 5-50%, of the additive.

The anthelmintic compound may be a mixture of anthelmintic compounds, e.g. a plurality of those specifically named above.

Suitably the present composition contains 1-10% by weight of the compound. A preferred embodiment comprises a method of combating helminthic parasites in an animal especially a non-human mammalian animal, which method comprises applying to the skin of the animal an anthelmintic amount of a composition which is a solution or suspension of 1-10% by weight of the compound in a carrier.

Usually the compound is applied just to the body of the animal, conveniently only to its back, preferably only to a small portion of its back. Thus, when a liquid composition is employed, it can simply be poured on to the back of the animal. The volume of composition employed is generally 0.01-10 ml per kg body weight of the animal.

The dosage rate depends on such factors as the particular compound and any carrier employed, the toxicity of the compound, the treatment desired and the animal treated. In general, however, the composition is applied at a rate of 1-250, preferably 1-100, especially 5-50, mg of the compound per kg body weight of the animal. For the larger mammals a suitable dose is 150-1,500 mg. A single dose may be sufficient, or it may be repeated if necessary.

The composition may be in unit dosage form e.g. individual capsules. It is desirably sterile. It may be prepared by admixing the ingredients.

The invention is illustrated by the following Examples, in which concentrations of active compounds are in g per 100 ml, solvent mixtures are expressed by volume, parts and percentages are by weight unless otherwise indicated, and temperatures are in degrees Centigrade unless otherwise indicated. As is common, amounts of 2,3,5,6-tetrahydro-6-phenylimidazo(2,1-b)thiazole or a salt thereof are of the racemic mixture unless otherwise stated.

EXAMPLE 1

Two sheep, each weighing 25 kg, were both infected with liver flukes (*Fasciola hepatica*) and stomach nematodes (*Haemonchus contortus*). One of the sheep was then treated with 0.625 g of 4,5,6-trichloro-7-(diethylsulphamoyl)-2-(trifluoromethyl)benzimidazole by pouring 21 ml of a 3% solution in aromatic hydrocarbon fraction of boiling range 180°-220° C. ("Solvent 200") along the mid-line of the back. The other sheep was treated with solvent alone.

One week later, the two sheep were killed and examined. No worms of either species were found in the sheep treated with the benzimidazole derivative whereas heavy burdens of both species were found in the sheep treated with solvent alone.

EXAMPLES 2

Two calves, each weighing 100 kg, were both infected with liver flukes (*Fasciola hepatica*). One of the calves was then treated with 2 g of 4,5,6-trichloro-7-(diethylsulphamoyl)-2-(trifluoromethyl)benzimidazole by pouring 67 ml of a 3% solution in aromatic hydrocarbon fraction ("Solvent 200") along the mid-line of the back. The other calf was treated with solvent alone.

One week later, the two calves were killed and examined. No flukes were found in the bile duct of the calf treated with the benzimidazole derivative whereas 75 flukes of all growth stages were recovered from the calf treated with solvent alone.

EXAMPLES 3-8

Eight sheep, each previously infected with 300 metacercaria of the liver fluke (*Fasciola hepatica*), were treated by pouring along the mid-line of the back (with the fleece parted) a 5% solution of 4,5,6-trichloro-7-(diethylsulphamoyl)-2-(trifluoromethyl)benzimidazole in a solvent consisting of a mixture of 4 parts of amyl alcohol and 1 part of dimethyl sulphoxide. The volume of solution used was adjusted to give dosage rates as indicated in the table below.

After 13 weeks, the sheep were killed and the livers examined. The number of live worms in the liver was noted and is tabulated below.

| Sheep number | Dosage (mg/kg) | No. of flukes | Mean no. of flukes | % Reduction |
| --- | --- | --- | --- | --- |
| 1 | 200 | 0 | 0.5 | 100 |
| 2 | 200 | 1 | | |
| 3 | 100 | 1 | 1.0 | 99 |
| 4 | 100 | 1 | | |
| 5 | 50 | 0 | 49.0 | 64 |
| 6 | 50 | 98 | | |
| 7 | control | 142 | 135 | — |
| 8 | control | 128 | | |

EXAMPLES 9-14

Three-week-old rats (Wistar strain) were infected orally with 30 metacercaria of the liver fluke, *Fasciola hepatica*. After 45 days, when most of the flukes were established in the bile duct, the rats were treated dermally by applying to their backs a 3% solution of 4,5,6-trichloro-7-(diethylsulphamoyl)-2-(trifluoromethyl)-benzimidazole in various solvents at dosage rates indicated below. Six days later the rats were killed and the bile duct dissected to determine the number of mature flukes surviving. The percentage reduction of flukes by comparison with controls treated with solvent alone is tabulated below, each result being the mean of four rats.

| Solvent | Dosage (mg/kg) | % Fluke Reduction |
| --- | --- | --- |
| 80% isopropanol + 20% dimethyl sulphoxide | 100 | 80 |
| 50% aromatic hydrocarbon ("Solvent 200") + 50% dimethyl sulphoxide | 150 | 85 |
|  | 100 | 80 |
|  | 50 | 65 |
| 25% aromatic hydrocarbon ("Solvent 200") + 75% dimethyl sulphoxide | 100 | 85 |
|  | 50 | 60 |

EXAMPLES 15 AND 16

Three-week-old rats (Wistar strain) were infected orally with 30 metacercaria of the liver fluke (*Fasciola hepatica*). After 37 days, the rats were infected intraperitoneally with 400 $L_3$ larvae of the *Nippostrongylus brasiliensis*. Eight days later, when most of the flukes had become established in the bile duct and the nematodes had become established in the small intestine, the rats were treated with a mixture of 4,5,6-trichloro-7-(diethylsulphamoyl)-2-(trifluoromethyl)benzimidazole (A) and 2,3,5,6-tetrahydro-6-phenylimidazo[2,1-b]thiazole (B). The treatment was carried out by pouring on to the back of the rats a mixture of a 2% solution of A in dimethyl sulphoxide and a 1% solution of B in dimethyl sulphoxide. Two rates of application were used, equivalent to (100 mg A + 50 mg B) per kg body weight and (100 mg A + 25 mg B) per kg body weight.

Six weeks after application, the rats were killed and counts were made of the number of nematodes surviving in the small intestine and the number of mature flukes surviving in the bile duct. The percentage reduction of worms by comparison with controls treated with solvent alone is tabulated below, each result being the mean obtained from the 4 rats used.

| Dosage rate | % reduction F. hepatica | % reduction N. brasiliensis |
| --- | --- | --- |
| (100 mg A + 50 mg B)/kg | 60 | 100 |
| (100 mg A + 25 mg B)/kg | 50 | 97 |

EXAMPLE 17

Sheep weighing 16 to 28 kg infected with the stomach nematode *Haemonchus contortus* were treated by pouring along the mid-line of the back a 5% solution of 2,3,5,6-tetrahydro-6-phenylimidazo[2,1,-b]thiazole in a solvent consisting of 20% dimethyl sulphoxide and 80% amyl alcohol. Application was made at rates equivalent to 100, 50 and 25 mg of the compound per kg body weight. The faeces passed over the following 24 hours were collected and examined. All were found to be free of nematode eggs whereas those passed by sheep treated with solvent alone were severely infected.

EXAMPLES 18 AND 19

Tests were carried out as in Examples 9-14 using other anthelmintics. Results are as follows:

| Anthelmintic | Solvent | dose (mg/kg) | % Fluke reduction |
| --- | --- | --- | --- |
| 4-hydroxy-3-iodo-5-nitrobenzonitrile | dimethyl sulphoxide | 100 | 67 |
|  |  | 50 | 54 |
| 3'-chloro-4'-(p-chlorophenoxy)-3,5-diiodosalicylanilide | dimethyl sulphoxide | 50 | 97 |
|  |  | 25 | 83 |

EXAMPLES 20-26

Three-week-old rats (Wistar strain) were infected intraperitoneally with 200 $L_3$ larvae of the nematode *Nippostrongylus bbrasilienis*. After eight days, when the worms had become established in the small intestines, the rats were treated dermally by applying a solution or suspension of an anthelmintic to the back of the animal. The nature of the anthelmintics and the solvent and concentration are listed below.

Four days later, the rats were killed and the small intestines removed to determine the number of worms surviving. The percentage reduction of worms by comparison with rats treated with solvent alone is tabulated below, each result being the mean of four rats.

| Anthelmintic | Concentration | Solvent | Dosage (mg/kg) | % worm reduction |
| --- | --- | --- | --- | --- |
| 2,3,5,6-tetrahydro-6-phenylimidazo/2,1-b/thiazole | 1% | dimethyl sulphoxide | 50 | 100 |
|  |  |  | 25 | 100 |
| 2-(2-methoxyethyl)-pyridine | 3% | 20% dimethyl sulphoxide + 80% amyl alcohol | 1000 | 100 |
| 2-(4-thiazolyl)benzimidazole | 3% suspension | 20% dimethyl sulphoxide + 80% amyl alcohol | 200 | 100 |
| methyl 5-butylbenzimidazole-2-carbamate | 3% suspension | 20% dimethyl sulphoxide + 80% amyl alcohol | 100 | 91 |
| methyl 1-(butylcarbamoyl)benzimidazole-2-carbonate | 5% | 20% dimethyl sulphoxide + 80% amyl alcohol | 750 | 100 |
|  |  |  | 94 | 86 |
| methyl benzimidazole-2-carbamate | 5% | 20% dimethyl sulphoxide + 80% amyl alcohol | 750 | 100 |
|  |  |  | 94 | 50 |
| diethyl 4,4'-o-phenylenebis(3-thioallophanate) | 7.5% | 20% dimethyl sulphoxide + 80% amyl alcohol | 750 | 100 |

EXAMPLE 27

Three-week-old rats (Wistar strain) were infected orally with 30 metacercaria of the liver fluke, [Fasciola hepatica. After 45 days, when most of the flukes were established in the bile duct, the rats were treated dermally with hexachlorophene at a dose of 100 mg/kg. This was applied to their backs as a 3% solution of 2,2'-methylenebis(3,4,6-trichlorophenol) in a 20%-80% mixture of dimethyl sulphoxide and amyl alcohol. Six days later the rats were killed and the bile dissected to determine the number of live flukes present. The percentage reduction of flukes by comparison with controls treated with solvent alone was 67%.

EXAMPLE 28

A sheep previously infected with 500 metacercaria of the liver fluke *Fasciola hepatica* was treated dermally 12 weeks later with oxyclozanide at a dose rate of 200 mg/kg. This was applied to the mid-line of the back (with fleece parted) as a 10% solution of 3,3',5,5',6-pentachloro-2,2'-dihydroxybenzanilide in a 20%-80% mixture of dimethyl sulphoxide and amyl alcohol. The sheep was slaughtered 6 days after treatment and the bile duct examined for liver flukes. 102 dead flukes were recovered compared with 196 and 279 live flukes from controls treated with solvent alone.

EXAMPLES 29-31

Sheep were infected with 2500 *Haemonchus contortus* infective larvae. Five weeks later dermal treatments were administered as shown in the table below, using (A) a 3% aqueous solution of 2,3,5,6-tetrahydro-6-phenylimidazo-[2,1-b]thiazole hydrochloride and (B) a 5% solution of 2,3,5,6-tetrahydro-6-phenylimidazo[2,1-b]thiazole base in a mixture of 20%-80% dimethyl sulphoxide and amyl alcohol. Treatments were assessed by carrying out foecal egg counts.

| Example | Dose mg/kg | Formulation | Foecal egg count/g Day of Treatment | 4 Days after Treatment |
|---|---|---|---|---|
| 29 | 25 | B | 6750 | 0 |
| 30 | 50 | B | 7900 | 0 |
| 31 | 100 | A | 24950 | 21400 |

EXAMPLE 32 AND 33

Three-week-old rats (Wistar strain) were infected orally with 30 metacercaria of the liver fluke, *Fasciola hepatica*. After 45 days the rats were treated dermally with 4,5,6-trichloro-7-(diethylsulphamoyl)-2-(trifluoromethyl)benzimidazole at a dose rate of 100 mg/kg. This was applied to their backs as a 3% solution in an aromatic hydrocarbon fraction ("Solvent 200") containing either (A), 10% of a polyisobutene ("Hyvis") or (B), 10% of lanolin. Six days later the rats were killed and dissected to determine the number of live flukes present. Results are given in the table below:

| Example | Dose mg/kg | Formulation | % Reduction |
|---|---|---|---|
| 32 | 100 | A | 70 |
| 33 | 100 | B | 55 |

EXAMPLE 34

Three-week-old rats (Wistar strain) were infected orally with 30 metacercaria of the liver fluke, *Fasciola hepatica*. After 45 days, when most of the fluke were established in the bile duct, the rats were treated dermally with 4,5,6-trichloro-7-(diethylsulphamoyl)-2-(trifluoromethyl)benzimidazole at a dose rate of 150 mg/kg applied to their backs as a 3% solution in a 50%—50% mixture of aromatic hydrocarbon fraction ("Solvent 200") and peanut oil. Six days later the rats were killed and the bile dissected to determine the number of live flukes present. The percentage reduction of flukes by comparison with controls treated with solvent alone was 50%.

EXAMPLES 35-38

Three-week-old rats (Wistar strain) were infected orally with 30 metacercaria of the liver fluke, *Fasciola hepatica*. After 45 days, when most of the flukes were established in the bile duct, the rats were treated dermally with the organobismuth compounds identified below at a dose rate of 188 mg/kg (and, in one case, 94 mg/kg) applied to their backs as a 3% solution in a 20%-80% mixture of dimethyl sulphoxide and amyl alcohol. Six days later the rats were killed and the bile dissected to determine the number of live flukes present. The percentage reduction of flukes by comparison with controls treated with solvent alone is tabulated below:

| Compound | Rate | % fluke reduction |
|---|---|---|
| Triphenylbismuth | 188 mg/kg | 80 |
| Triphenylbismuth dinitrate | 188 mg/kg | 85 |
| Triphenylbismuth dichloride | 188 mg/kg | 60 |
| Triphenylbismuth difluoride | 188 mg/kg | 95 |
|  | 94 mg/kg | 90 |

EXAMPLE 39

Three-week-old rats (Wistar strain) were infected intraperitoneally with 200 $L_3$ larvae of the nematode *Nippostrongylus brasiliensis*. After eight days, when the worms had become established in the small intestines, the rats were treated dermally by applying a 3% solution of 4,5,6-trichloro-7-(methylsulphamoyl)-2-(trifluoromethyl)benzimidazole in a solvent consisting of 20% dimethyl sulphoxide and 80% amyl alcohol to the back of the animal at rates of 94 mg/kg and 46 mg/kg of active ingredient/body weight.

Four days later, the rats were killed and the small intestines removed to determine the number of worms surviving. The percentage reduction of worms by comparison with rats treated with solvent alone is tabulated below, each result being the mean of three rats.

| Rate of application | % worm reduction |
|---|---|
| 94 mg/kg | 91 |
| 46 mg/kg | 65 |

EXAMPLE 40

Following the procedure of Example 20, except that instead of the racemate of 2,3,5,6-tetrahydro-6-phenylimidazo(2,1-b)thiazole half the dosage of just the laevo isomer was employed, gave similar results.

We claim:

1. A pour-on veterinary composition useful for the treatment of helminthic infestations in animals, which consists essentially of an anthelminthically effective amount of tetramisole or levamisole or a non-toxic acid addition salt thereof in combination with one or more of paraffins of 6 to 20 carbon atoms, halogenated aliphatic hydrocarbons, ketones, ethers, amides, sulphones or sulphoxides, as a diluent suitable for pour-on therapy.

2. A composition according to claim 1 wherein said diluent is a paraffin of 6 to 20 carbon atoms.

3. A composition according to claim 1 wherein the diluent is a halogenated aliphatic hydrocarbon.

4. A composition according to claim 3 wherein the halogenated aliphatic hydrocarbon is a carbon tetrachloride.

5. A composition according to claim 1 wherein the diluent is a ketone.

6. A composition according to claim 5 wherein the ketone is cyclohexanone or 2-butanone.

7. A composition according to claim 1 wherein the diluent is an ether.

8. A composition according to claim 7 wherein the ether is di-isopropyl ether or tetrahydrofuran.

9. A composition according to claim 1 wherein the diluent is an amide.

10. A composition according to claim 9 wherein the amide is dimethylformamide.

11. A composition according to claim 1 wherein the diluent is a sulphone.

12. A composition according to claim 11 wherein the sulphone is dimethyl sulphone or sulpholane.

13. A composition according to claim 1 wherein the diluent is a sulphoxide.

14. A composition according to claim 13 wherein the diluent is dimethylsulphoxide.

15. A composition according to claim 14 which additionally contains amyl alcohol.

16. A composition according to claim 1 which additionally contains a surface active agent.

17. A method for treating helminthic infestations in animals which comprises pouring on to the external skin of the animal to be treated an effective amount of the composition according to claim 1.

* * * * *